United States Patent
Corboy, Jr.

(10) Patent No.: US 12,290,525 B2
(45) Date of Patent: May 6, 2025

(54) 5 ALPHA DIHYDROTESTOSTERONE FORMULATIONS AND ASSOCIATED METHODS OF USE AND TREATMENT

(71) Applicant: Edward Dunne Corboy, Jr., Skokie, IL (US)

(72) Inventor: Edward Dunne Corboy, Jr., Skokie, IL (US)

( * ) Notice: Subject to any disclaimer, the term of this patent is extended or adjusted under 35 U.S.C. 154(b) by 0 days.

(21) Appl. No.: 18/702,485

(22) PCT Filed: Dec. 5, 2023

(86) PCT No.: PCT/US2023/082601
§ 371 (c)(1),
(2) Date: Apr. 18, 2024

(87) PCT Pub. No.: WO2024/123833
PCT Pub. Date: Jun. 13, 2024

(65) Prior Publication Data
US 2024/0307410 A1  Sep. 19, 2024

Related U.S. Application Data

(60) Provisional application No. 63/430,320, filed on Dec. 5, 2022.

(51) Int. Cl.
| | | |
|---|---|---|
| A61K 31/568 | (2006.01) | |
| A61K 9/00 | (2006.01) | |
| A61K 9/06 | (2006.01) | |
| A61K 9/48 | (2006.01) | |
| A61K 47/10 | (2017.01) | |
| A61K 47/14 | (2017.01) | |
| A61K 47/18 | (2017.01) | |
| A61K 47/32 | (2006.01) | |

(52) U.S. Cl.
CPC .......... *A61K 31/568* (2013.01); *A61K 9/0014* (2013.01); *A61K 9/0053* (2013.01); *A61K 9/06* (2013.01); *A61K 9/48* (2013.01); *A61K 47/10* (2013.01); *A61K 47/14* (2013.01); *A61K 47/18* (2013.01); *A61K 47/32* (2013.01)

(58) Field of Classification Search
CPC .. A61K 31/568; A61K 9/0014; A61K 9/0053; A61K 9/06; A61K 9/48; A61K 47/10; A61K 47/14; A61K 47/18; A61K 47/32
See application file for complete search history.

(56) References Cited

U.S. PATENT DOCUMENTS

| | | | |
|---|---|---|---|
| 9,987,213 B2 * | 6/2018 | Corboy, Jr. | ............ A61K 45/06 |
| 10,307,359 B2 | 6/2019 | Corboy, Jr. | |
| 10,307,360 B2 | 6/2019 | Corboy, Jr. | |
| 11,020,336 B2 | 6/2021 | Corboy, Jr. | |
| 11,833,238 B2 | 12/2023 | Corboy, Jr. | |
| 12,029,741 B1 | 7/2024 | Corboy, Jr. | |
| 2013/0122085 A1 | 5/2013 | Dalton et al. | |

FOREIGN PATENT DOCUMENTS

| | | | | |
|---|---|---|---|---|
| WO | 2022120054 | | 6/2022 | |
| WO | WO-2022120054 A1 | * | 6/2022 | ........... A61K 31/568 |

OTHER PUBLICATIONS

PubChem CID 10635, Androstanolone. (Year: 2004).*
The Trevor Project. Gender Identity. (Oct. 2019) . . . https://www.thetrevorproject.org/wp-content/uploads/2021/08/Trevor-Project-Gender-Identity-Research-Brief_October.pdf (Year: 2019).*
World Health Organization https://www.who.int/standards/classifications/frequently-asked-questions/gender-incongruence-and-transgender-health-in-the-icd#:~:text=What%20is%20gender%2Daffirmative%20health,affirm%20an%20individual's%20gender%20identity (Year: 2024).*
Finlayson C, Jameson J, Achermann JC. Sex Development. In: Loscalzo J, Fauci A, Kasper D, Hauser S, Longo D, Jameson J. eds. Harrison's Principles of Internal Medicine, 21e. McGraw-Hill Education . . . (cont'd below) (Year: 2022).*
Finlayson C,, et al . . . https://accessmedicine.mhmedical.com/content.aspx?bookid=3095&sectionid=265 (Year: 2022).*
Meriggiola MC, et. al. Effects of testosterone undecanoate administered alone or in combination with letrozole or dutasteride in female to male transsexuals. J Sex Med. Oct. 2008;5(10):2442-53. doi: 10.1111/j.1743-6109.2008.00909.x. Epub 2008 (Year: 2008).*
International Search Report and Written Opinion corresponding to International Patent Application No. PCT/US2023/082601, mailed Mar. 13, 2024.
Forti et al., "Effects of Pharmacological Doses of Testosterone and Dihydrotestosterone on the Hypothalamic-Pituitary Axis Function of Klinefelter Patients", Journal of Endocrinological Investigation, Apr. 1, 2014, vol. 6, pp. 297-300.
Motosko CC, Tosti A. Dermatologic Care of Hair in Transgender Patients: A Systematic Review of Literature, Dermatol Ther (Heidelb). Oct. 2021;11(5):1457-1468).
Coleman, E., et al., (2022). Standards of Care for the Health of Transgender and Gender Diverse People, Version 8. International Journal of Transgender Health, 23(S1), S1-S260.

(Continued)

Primary Examiner — Clinton A Brooks
Assistant Examiner — Josmalen M. Ramos-Lewis
(74) Attorney, Agent, or Firm — McAndrews, Held & Malloy, Ltd.

(57) ABSTRACT

Disclosed are pharmaceutical and cosmetic compositions that include 5 Alpha Dihydrotestosterone (or alternatively, 5α-DHT, 5 Alpha-DHT, 5 Alpha DHT, 5a-DHT, DHT), and associated methods of use and treatment that can be used alone or in combination with other treatments to provide, improve, or promote general well-being and health, including mental health, in a subject. In particular the compositions, methods, and uses can provide, promote, support, and/or improve outcomes associated with gender reassignment, gender transitioning, and/or gender-affirming therapy in a subject who may be in need thereof.

17 Claims, No Drawings

(56) References Cited

OTHER PUBLICATIONS

Swerdloff RS, Dudley RE, Page ST, Wang C, Salameh WA. Dihydrotestosterone: Biochemistry, Physiology, and Clinical Implications of Elevated Blood Levels. Endocr Rev. Jun. 1, 2017;38(3):220-254. doi: 10.1210/er.2016-1067. PMID: 28472278; PMCID: PMC6459338.

* cited by examiner

5 ALPHA DIHYDROTESTOSTERONE FORMULATIONS AND ASSOCIATED METHODS OF USE AND TREATMENT

CROSS REFERENCE TO RELATED APPLICATIONS

The present application is a National Phase Entry of PCT International Application No. PCT/US2023/082601 which was filed on Dec. 5, 2023, which is related to, and claims priority to, U.S. Provisional Patent Application Ser. No. 63/430,320, filed Dec. 5, 2022, both of which are hereby incorporated by reference in their entireties.

FIELD

The disclosure provides compositions that include 5 Alpha Dihydrotestosterone (or alternatively, 5α-DHT, 5 Alpha-DHT, 5a-DHT, DHT), including pharmaceutical and cosmetic formulations and associated methods of use and treatment. The compositions and methods can be used alone, concurrently or in fixed combination with other medicines, hormones, or therapies and/or surgery, for any number of treatments including cosmetic, therapeutic, and combination applications. The disclosed methods and uses can provide, improve, or promote general well-being and health, including mental health, in a subject. The disclosed methods and uses can provide, promote, support, improve outcome, and/or are associated with, gender reassignment, gender transitioning, and/or gender-affirming therapy (e.g., surgical and/or hormone therapy) in a subject, for example, any subject who may have, be, and/or identify as lesbian, gay, bisexual, transgender, cis-gender, queer, indeterminate sex or intersex, or non-binary (LGBTQI+) of any age. Some particular methods and compositions can promote hair growth in such subjects (e.g., on facial, head, body, and/or pubic regions) and can provide for overall increased medical health, wellness and mental health.

BACKGROUND

Human beings who make up and/or identify as a member of the community of lesbian, gay, bisexual, transgender, queer and intersex (LGBTQI+) and non-binary people, make up an important global human community ("the Community") and they have important healthcare needs, gender related sociological needs, mental health needs, and legal protections. Their needs have been addressed increasingly by the medical, scientific and mental health, sexual health communities, as well as by political leadership of many countries and territories around the world, and some religious organizations.

The term "LGBTQI+" is an acronym that is typically inclusive of lesbian, gay, bisexual, transgender, and queer or questioning and intersex human beings of any age. The 'plus' sign ("+") refers to the many other self-identifications under the umbrella of 'sexuality' and/or 'gender' that has, and continues to, evolved over time to include more people who feel that they do not fall within one or the other 'identified' groups. Thus, LGBTQI+ is an umbrella term that encompasses the spectrum of people who are not, or do not identify as, heterosexual and whose gender identities, sexual preferences/attraction, and the like may be variable, non-binary and include a wide variety of identities, preferences, interests, and orientations.

The terms non-binary (or nonbinary, non binary, etc.) and/or genderqueer are typically used as umbrella terms by persons to describe and identify their gender identity that are outside the usual gender binary of male and female-identities that are fluid and/or possess a mixed set of characteristics and preferences.

The transgender community includes a complex community of human beings. The Center for American Progress ("CAP") is operated as a public charity. It is located in Washington, DC in the United States. It has received official IRS recognition of its tax exempt status under sections 501(c)(3) and 509(a)(1) of the Internal Revenue Code. The CAP website noted the following on Dec. 1, 2022 (internal citations omitted): "The term 'Transgender' is an umbrella term used to describe people whose gender identity and/or gender expression differ based on the sex they were assigned at birth. The transgender community is not a monolith. Transgender people have diverse sexual orientations, gender expressions, and gender identities, and transgender identities do not depend on physical appearance or medical procedures. Discrimination, stigma, and violence, along with other social, political, and economic factors, significantly affect the physical, mental, and behavioral health of transgender adults. Research studies report that, compared with the general population, transgender people suffer from more chronic health conditions and experience higher rates of health problems related to HIV/AIDS, substance use, mental illness, and sexual and physical violence, as well as higher prevalence and earlier onset of disabilities that can also lead to health issues. In addition to poorer health outcomes, transgender people also encounter unique challenges and inequalities in their ability to access health insurance and adequate care. The public health and economic crises spurred by the COVID-19 pandemic have only exacerbated existing disparities and barriers to care for transgender people, especially transgender people of color."

The CAP website further notes that transgender individuals are a high-risk population for mental and physical and medical health problems and are consistently and systemically underserved by the American medical system and many global health systems. Societal pressures regularly contribute to high rates of stress and can make increase the likelihood of poor health outcomes for transgender individuals. The website notes the 2019 Behavioral Risk Factor Surveillance System (BRFSS) data, in which 60 percent of the transgender respondents had experienced poor mental health at least one day in the past month (about 23 percent higher than that of cisgender respondents); 54 percent report poor physical health at least one day in the past month (about 18 percent higher than that of cisgender respondents); as well as having increased likelihood of developing conditions such as cardiovascular disease, asthma, chronic depression, sexually transmitted infection, and HIV.

The disclosure addresses these particular health needs and challenges by providing pharmaceutical compositions, therapies, and methods of use and/or treatments that can address and provide relief to patients who fall within the LGBTQI+ Community and non-binary Community, and in some particular aspects and embodiments, to transgender and transsexual human beings of any age. The disclosure relates to therapies that can benefit one or both of female to male transgender populations, as well as male to female transgender populations, and non-binary populations, of any age. The disclosure also relates to therapies that can benefit transgender and transsexual human males (i.e., "female to male") at any age and also to patients with Klinefelter Syndrome (XXY genetics), a genetic and rare disease, associated with androgen insensitivity disorders listed on the NIH of the U.S. Government website.

SUMMARY

In an aspect the disclosure relates to a method of treating a patient receiving gender affirming hormone therapy comprising administering 5 Alpha-DHT to the patient in an amount effective to promote or enhance overall health, mental health, physical aesthetics, and/or hair growth.

In an aspect the disclosure relates to a method of supportive medical treatment in a patient receiving gender affirming hormone therapy comprising administering 5 Alpha-DHT to the patient in an amount effective to promote or enhance overall health, mental health, physical aesthetics, and/or hair growth.

In an aspect the disclosure relates to a method of treating a patient who is seeking to transition or modify their physical appearance comprising administering 5 Alpha-DHT to the patient in an amount effective to modify their physical appearance.

In some embodiments, the method treats a patient who is or identifies as a transgender person or a transsexual person or a non-binary person.

In some embodiments, the method promotes intermediate and terminal hair growth on one or more regions of the body of the patient as part of gender affirming or gender transitioning therapy.

In an aspect the disclosure relates to the use of a composition or pharmaceutical formulation comprising 5 Alpha-DHT as part of a gender affirming therapy or a gender transitioning therapy.

In embodiments, the use can be in combination with one or more of androgens, other hormones, active agents, surgery, and mental health support therapies.

In embodiments, the use or method improves or enhances an existing therapy comprising testosterone.

In embodiments, the use or method induces levels of androgen hormone in central nervous system to levels that can increase mental alertness, mood, and overall brain function in a patient undergoing treatment.

In embodiments, the use or method promotes bone health, prevents osteoporosis, and/or treats osteoporosis or osteopenia in a patient undergoing treatment.

In embodiments, the use or method improves serum level of 5 Alpha-DHT in a patient undergoing treatment.

In embodiments, the use or method improves cardiovascular health in a patient undergoing treatment.

In an aspect, the disclosure relates to a method for supportive gender affirming therapy in a patient in need thereof, comprising administering 5 Alpha Dihydrotestosterone (5 Alpha-DHT), or a pharmaceutically acceptable salt or ester thereof, to the subject.

In embodiments of the above aspects, the use or method induces one or more physiological characteristics associated with the gender to which the patient is affirming or transitioning.

In embodiments, the use or method wherein the method further promotes or enhances the patient's overall health, mental health, aesthetics, or hair growth on the face, body, or pubic region.

In embodiments of the above aspects, the administering of 5 Alpha-DHT is in combination with one or more other therapy. In embodiments, the other therapy comprises a hormone therapy and/or surgery.

In embodiments of the above aspects, the patient is transgender or transsexual.

In embodiments of the above aspects, the 5 Alpha-DHT is administered systemically. In some embodiments, the 5 Alpha-DHT is administered orally, topically, transmucosally, by injection, by suppository transdermally, or by implant.

In embodiments of the above aspects, the method or use promotes hair growth on the face, body, or pubic region of the patient.

In embodiments of the above methods and uses, the 5 Alpha-DHT is administered once a day.

In embodiments of the above methods and uses, the 5 Alpha-DHT is administered on an interval therapy dosing cycle comprising at least one period of administration a period of non-administration. In some embodiments, the interval therapy comprises an administration period of 1-4 weeks followed by at least 1 week of non-administration.

Other aspects and embodiments falling within the scope of the disclosure will become apparent to those of skill in the art in light of the description and claims that follow.

DETAILED DESCRIPTION

In a general sense, the disclosure provides pharmaceutical formulations, method of use, methods of treatment, and methods of supportive treatment comprising 5 Alpha Dihydrotestosterone (5α-DHT, 5 Alpha-DHT, 5a-DHT, DHT) alone or in fixed combination, with other, medicines, hormones, or therapies and/or surgery. In particular embodiments, the disclosure provides formulations, methods of use, methods of treatment and methods of supportive treatment for patients in need of, or in patients who wish to pursue, gender affirming hormone therapy. In embodiments, the patients may be, or may identify as, lesbian, gay, bisexual, transgender, queer and intersex (LGBTQI+) and non-binary, and may be of any age. In various embodiments, the methods can promote or enhance overall health, mental health, general wellness, aesthetics, hair growth of facial, body and pubic hair.

Definitions

The terms "effective amount", "therapeutically effective amount" or "pharmaceutically effective amount" as used herein refers to that amount of the therapeutic agent sufficient to ameliorate or achieve desired pharmaceutical therapy results of one or more aspects of the disorders that the patient and physician seek to treat. The result can be reduction and/or improvement and/or alleviation of the signs, symptoms, or causes of a disease, or any other desired alteration of a biological and human health systems. For example, an "effective amount" for therapeutic uses is the amount of the composition comprising an agent as set forth herein required to provide a clinically significant decrease in an LGBTQI+ or non-binary conditions, health problems and/or diseases. For example, for the given aspect (e.g., length of incidence), a therapeutically effective amount will show an increase or decrease of at least 1%, 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control. An appropriate "effective" amount in any individual case may be determined using techniques, such as a dose escalation study.

"Treating" and "treatment" as used herein include therapeutic treatments of active health problems and/or prophylactic treatments. Treatment methods include administering to a subject a therapeutically effective amount of an active agent. The administering step may consist of a single administration or may include a series of administrations that may occur over a single day or period of days or longer periods of time. The length of the treatment period depends on a variety of factors, such as the severity and the number of the health conditions, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art as well as based on patient feedback, healthcare history taking and physical evaluation of health problems, health issues, health disorders, aesthetic disorders, and/or disease states. In some instances, chronic administration may be required. For example, the compositions are administered to the subject in an amount and for a duration sufficient to treat the patient and seek to achieve desired positive treatment effects.

Treatment is inclusive of beneficial or desired results in a subject's condition with regard to cosmetic or aesthetic results/appearance and can include, but is not limited to, alleviation or amelioration of one or more physical appearances or conditions, diminishment of the extent of one or more physical appearances or conditions, stabilizing mood and/or mental health, promoting or preventing one or more physical appearances or conditions, delay or slowing progression of one or more physical appearances or conditions, promoting or increasing progression of one or more physical appearances or conditions, and the like.

As used herein, "topical application," "topical administration," and "topically administering" are used interchangeably herein and include the administration of a composition to the skin of the body, the abdomen, the chest, the back, the shoulder area including the arms, the leg areas, the axilla, the scalp, upper and/or lower eyelid margin, eyebrow region, scalp or face as well as the beard and mustache area of the face and neck. Topical application or administering may result in the delivery of an active agent to the eyebrows or skin or a localized region of the skin on the human body.

"Topical formulation" and "topical pharmaceutical composition" are used interchangeably herein and include a formulation that is suitable for topical application to the skin of any area the skin of the body, the penis, the clitoris, the urethra via pellet formulations, the face, beard hair and mustache growth areas above or close to the upper lip of the mouth the arms, the abdomen, the axilla, the back, or chest areas. Specific topical formulations can be used for topical, local, regional, or transdermal application of substances.

The abbreviations used herein have their conventional meaning within the chemical, biological or pharmaceutical arts.

The terms "about" and "approximately equal" are used herein to modify a numerical value and indicate a defined range around that value. If "X" were the value, "about X" or "approximately equal to X" would generally indicate a value from 0.90X to 1.10X. Any reference to "about X" minimally indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%." "About" may also include variations in the amount that a regulatory body such as the FDA or EMEA would view as bioequivalent to the claimed amount.

As used herein, the phrase "pharmaceutically acceptable salts" refers to salts of the active compound(s) which possess the same pharmacological activity as the active compound(s), and which are neither biologically nor otherwise undesirable. A salt can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, naturally and synthetically derived amino acids.

Non-limiting examples of base salts include ammonium salts; alkali metal salts, such as sodium and potassium salts; alkaline earth metal salts, such as calcium and magnesium salts; salts with organic bases, such as dicyclohexylamine salts; methyl-D-glucamine; and salts with amino acids, such as arginine, lysine, and so forth. Also, the basic nitrogen-containing groups can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others.

"Prodrugs" refer to compounds which are a precursor of a compound and that is converted into its active form within the skin, and/or hair follicles and/or the body, for example, in the body by normal or scientifically recognized metabolic processes. In some embodiments, esters of the active agent (i.e., Testosterone and/or 5 Alpha-DHT) is included within the term, "prodrug".

Alopecia of the scalp hair on the head (baldness) a highly complex scalp hair condition that is related to genetics and epigenetics of any given individual and occurs in disorders such as androgenetic alopecia, as well as other disorders of alopecia, and may be a deficiency of either normal or abnormal hair growth, hair maturation or loss of terminal hair follicles and hair is a major aesthetic and cosmetic problem in humans. Alopecia of the scalp hair on the head (baldness) is a deficiency or loss of terminal hair, and terminal hair follicles the broad diameter, colored hair that is readily seen. It occurs in both human males and females and can occur due to a number of medical and/or genetic or epigenetic issues in any given person. However, in the so-called bald person although there is a noticeable absence of terminal hair, the bald scalp skin may lose terminal hairs and contain more and more vellus hair which is a fine, small diameter hair shaft, and non pigmented or colorless hair which may require dermoscopy examinations and also microscopic examination to determine its presence. This vellus hair is a precursor to terminal hair. In some cases of scalp alopecia, hair follicles have been destroyed by the long term impact of 5 alpha reductase and the impact of dihydrotestosterone, and other factors in genetically and epigenetically vulnerable terminal hair follicles.

As used herein, "oral therapy drug delivery," and "oral administration," are used interchangeably herein and include the administration of a composition of 5 Alpha-DHT, 5 Alpha-DHT undeconoate or other androgens or metabolites of other androgens.

As used herein, "parenteral drug delivery," and "injectable administration drug delivery methods," are used interchangeably herein and include the administration of a composition of 5 Alpha-DHT, 5 Alpha-DHT undeconoate or other androgens or metabolites of other androgens.

In embodiments, the disclosure provides benefits of pharmaceutical androgen (including 5 Alpha-DHT) therapies that are part of a gender affirming health care treatment program under the direction of experts in medicine, physicians, nurse practitioners, psychologists, sexual medicine, gender medicine, psychiatry, psychology, and a wide range of experts in scientific fields related to sexual identity and gender identity therapies that may improve health, mental health, aesthetic appearance, hair growth of terminal hair and intermediate hair, and a host of psychological and/or psychiatric issues relating to happiness, joy, inner peace and a comfort level with and individuals gender identity and overall quality of their lives and overall health status.

The disclosure provides newly contemplated pharmaceutical therapies and methods of use, which may be of particular benefit to transgender and transsexual human beings of any age. The disclosed pharmaceutical therapies may be of particular benefit to transgender and transsexual human males who are referred to a "female to male" transgender children, boys, adolescents, or adult males. The present invention discloses novel therapies for use in both female to male transgender populations, of any age, and also discloses novel therapies for use in male to female transgender populations, of any age.

The global transgender community includes a highly diverse group of communities, and as a group, and as individuals, transgender humans of any age, can face additional challenges that "hetero-normative" or "cis" individuals do not typically face or experience. For example, some medical and mental health organizations, societies, psychological and psychiatric organizations, and their manuals for coding various forms of health and various psychological and psychiatric forms of illness or disorders of many kinds may consider members of the transgender community as suffering from an illness, regardless of the individual's current physiological or mental health. As such, members of the transgender community may experience a set of significant prejudicial influences that can create health-related challenges that individuals outside of that community are not exposed to and typically do not experience.

The U.S. Government office of Health and Human Services (HHS) Office of Population Affairs notes on their website: "Gender-affirming care is a supportive form of healthcare. It consists of an array of services that may include medical, surgical, mental health, and non-medical services for transgender and non-binary people. For transgender and non-binary children and adolescents, early gender affirming care is crucial to overall health and well-being as it allows the child or adolescent to focus on social transitions and can increase their confidence while navigating the healthcare system."

The HHS website notes: "Research demonstrates that gender-affirming care improves the mental health and overall well-being of gender diverse children and adolescents. Gender-affirming care is patient-centered and treats individuals holistically, aligning their outward, physical traits with their gender identity. Gender diverse adolescents, in particular, face significant health disparities compared to their cisgender peers. The website notes further that, "[t]ransgender and gender non-binary adolescents are at increased risk for mental health issues, substance use, and suicide" with 52 percent of those surveyed contemplating suicide within the past year. As such in order to achieve better outcomes for this population, it is important to provide safe and affirming healthcare.

As noted herein, the terms transgender and non-binary are used commonly as an umbrella term that includes diverse types of gender variant people (including transsexual people) that fall under the umbrella term of LGBTQI+ and non-binary human beings. Trans men have a male gender identity, and many trans men choose to undergo gender affirming surgical and/or hormonal transition, or both (i.e., sex reassignment therapy), to alter their appearance in a way that aligns with their gender identity or alleviates gender dysphoria.

The term "transsexual" is commonly used as an umbrella term that when used either as an adjective or a noun, for example:
   adj. Denoting or relating to a transgender person, especially one whose bodily characteristics have been altered through surgery or hormone treatment to bring them into alignment with their gender identity. Examples include "transsexual women", "transsexual men" and "transsexual human beings" of any age. "transsexual adolescents".
   n. A transgender person, especially one whose bodily characteristics have been altered through surgery or hormone treatment to bring them into alignment with their gender identity. This use may include a "a pre-operative male-to-female or female-to-male transsexual", and also a "post-operative male-to-female or female-to-male transsexual".

Common description of transsexual humans can include (as exemplified, e.g., by Wikipedia on Nov. 27, 2022): " . . . people [who] experience a gender identity that is inconsistent with their assigned sex, and desire to permanently transition to the sex or gender with which they identify, usually seeking medical assistance (including sex reassignment therapies, such as hormone replacement therapy and sex reassignment surgery) to help them align their body with their identified sex or gender". The reference notes that "transsexual" individuals are often considered a subset of "transgender" individuals, though that classification is not universally accepted among transsexual people. In some general instances it can be useful to identify and/or diagnose gender dysphoria when a person experiences marked and persistent incongruence between their experienced gender (their own sense of their gender) and their assigned sex.

It is noted that not all members of the transgender population or non-binary population (male or female or non-binary) seek or elect to pursue sexual affirmation or reassignment (e.g., reassignment surgery, treatment with gender affirming hormones) to transition toward what may be considered as a transsexual human being. A "trans man" or a "trans boy" is a man or boy who was assigned female at birth. The label of transgender man or boy is not always interchangeable with that of transsexual man, although the two labels are often used in this way.

As mentioned above, the term transsexual originated in the medical and psychological communities, and is generally considered a subset of transgender, although the two are not always interchangeable. In clinical application it predominantly describes people with medically diagnosed gender dysphoria who desire to permanently transition to the opposite sex via sex reassignment therapy, regardless of how the individual may prefer to identify themself. Transmasculine (or transmasc or transman) is typically used as a broader term for all trans individuals with predominantly masculine identities or gender expression, and includes trans men as well as non-binary people who were assigned female at birth and may have an identity that is partially masculine but not entirely male.

Individuals who identify as transsexual men and/or transgender men may seek medical interventions from licensed physicians and healthcare teams, which can include hormones and surgery to refine their bodies to be as congruent as possible with their gender identity and presentation. However, many transgender persons and transsexual (men or women) cannot afford to or choose not to undergo surgery or hormone replacement therapy.

A trans woman or a transgender woman is a woman who was assigned male at birth. Trans women have a female gender identity, may experience gender dysphoria, and may transition; this process commonly includes hormone replacement therapy and sometimes sex reassignment surgery, which can bring relief and resolve feelings of gender dysphoria.

As discussed above with regard to boys and men (males), when discussing girls and women (females), the term transgender is not always interchangeable with transsexual, regardless of common usage. Transgender is an umbrella term that typically includes different types of gender variant people (including transsexual people). Transwomen face significant discrimination in many areas of life, including in employment and access to housing, and face physical and sexual violence and hate crimes.

In various aspects, the disclosure provides for the improvement in overall health, mental health, and well-being in individuals who seek to transition or modify their physical appearance and aesthetics, including enhanced terminal hair growth in the beard and mustache areas, the chest and other parts of the body. The pharmaceutical formulations and compositions and methods of use can be used to modify, alter, align, and/or improve a subject's aesthetic and/or physical appearance, promote hair growth, improve overall general health and mental health, and other physical and psychological characteristics that can improve feelings of heath, well-being, contentment, self-worth, and mood.

In some aspects, the disclosed methods and compositions can promote intermediate and terminal hair growth on areas of the body of a subject as part of gender affirming care hormonal therapy or gender transitioning therapy.

In some aspects, the disclosed methods and compositions provide a subject with improved mental health and overall happiness and quality of life.

Any of the aspects and embodiments described herein may be delivered to subjects who have reached an age of consent such as, for example, adults who are 18 years of age or older. The aspects and embodiments described herein may be delivered to subjects who are less than legal age of consent (e.g., less 18 years of age) after substantial consideration, counseling, consultation by one or more healthcare experts, or interdisciplinary teams of healthcare experts, or specialists in one or more areas of psychology, psychiatry, surgery, sexual medicine, and transgender specialists, sexual medicine and the like.

While a myriad of therapeutic options are available to transgender patients, those options (individual interventions or combinations) may fall short of achieving the desired effect regarding masculinizing or feminizing hormonal therapy, especially with regard to the patients' hair. (see, Motosko C C, Tosti A. Dermatologic Care of Hair in Transgender Patients: A Systematic Review of Literature. Dermatol Ther (Heidelb). 2021 October; 11(5):1457-1468). The reference acknowledges that the relevance of dermatologic techniques becomes apparent, given that "altering patterns of hair growth continue[s] to play an integral part in the affirmation of gender in patients with gender dysphoria."

Nevertheless, there remain many longstanding unmet needs and for many of LGBTQI+ non-binary people. These unmet needs include, but are not limited to, a host of health problems, health disorders, recognized diseases, health disorders, mental health disorders, risk of depression and suicide, gender affirming health care and mental health care needs, aesthetic disorders, including hair growth therapies. As such, there is a need for compositions and therapeutic methods that can address these needs.

The Mayo Clinic Website refers to the use of testosterone as an androgen therapy; however it does not state any use or application of 5 Alpha-DHT therapy. The Mayo Clinic website notes that "(m)asculinizing hormone therapy involves taking the male hormone testosterone. It stops menstrual cycles and decreases the ovaries' ability to make estrogen. Masculinizing hormone therapy can be done alone or along with masculinizing surgery." As such, the guidance lacks discussion of 5 Alpha-DHT as a monotherapy or as part of a concurrent therapy, or fixed combination therapy to be used as part of a masculinizing therapy in individuals who are seeking such treatment (e.g., transgender human males, or any members of the LGBTQI+ and non-binary community).

In aspects, the disclosure relates to 5 Alpha-DHT formulations and methods that can greatly enhance therapeutic benefits and/or cosmetic benefits and efficacy relative to the benefits and effects that may be experienced with testosterone at least because 5 Alpha-DHT is a more potent androgen than testosterone with regard to androgenic activity. Thus, the compositions and methods disclosed herein that comprise 5 Alpha-DHT pharmaceutical therapies, and formulations, can provide greatly enhanced therapeutic and cosmetic aesthetic benefits, particularly for terminal hair growth, when used as a monotherapy or multiple concurrent androgen therapy treatment regiments under the care of a licensed physicians. In some embodiments, the benefits of the therapeutic use of systemic gender affirming testosterone (T) therapy are synergistically improved when used in combination with formulations of 5 Alpha-DHT to improve both human health, mental health, and aesthetics including the promotion of hair growth in multiple locations including but not limed to the beard, mustache, chest areas.

Compositions and Methods

In some aspects the disclosure provides a composition, including a pharmaceutical formulation, and related methods of treatment and/or use comprising 5 Alpha Dihydrotestosterone, (5α-DHT, 5 Alpha-DHT, DHT). In embodiments, the composition and/or method is used concurrently or in fixed combinations with one or more other androgens, other hormones, other medicine, surgery and mental health support therapies. In embodiments the composition and/or method comprises part of a gender affirming therapy and/or care that includes, but is not limited to, medical, pharmaceutical, hormonal, psychological, and/or surgical therapy (e.g., "gender affirming therapy") in an individual seeking such therapies. In embodiments, the individual may be or identify as a LGBTI+ and/or non-binary human. In some particular embodiments, the individual may be or identify as a transgender or transsexual human male.

In some aspects and embodiments the compositions and methods of use can promote, support, and/or improve one or more of general health, mental health, gender affirming hormone therapy in a patient who is or identifies as lesbian, gay, bisexual, transgender, queer and intersex (LGBTQI+) and nonbinary humans, of any age. In some particular embodiments, the pharmaceutical formulations compositions and methods of use can promote, improve, increase, and/or generate intermediate or terminal hair growth in one or more region of the body, including for example, facial, head, body and pubic regions.

In some aspects and embodiments, the disclosure provides a wide range of formulations including oral, topical, injectable, suppository and other recognized drug delivery routes. In such aspects and embodiments, the disclosure provides a wide range of dosing options that may be daily, or may be every other day or every few days, and includes interval therapy periods and cycles where 5 Alpha-DHT is administered for a period of time and then halted for a defined a period of time (a non-treatment interval), as an intermittent dosing regimen. Such a regimen can provide treatment benefits and can minimize side effects.

In some aspects, the disclosure relates to a method of use, or of treatment, comprising a 5 Alpha-DHT compositions or formulations. In some embodiments, the 5 Alpha-DHT comprises a formulation comprising 5 Alpha-DHT undeconoate (e.g., oral, topical, transmucosal, implantable/depot, or injectable, etc.), that may enhance libido in human males and females. In some embodiments, the route of application/delivery that may include topical application to one or more pubic region and/or the genitals.

The number of transgender female to male individuals seeking "cross-sex hormone therapy" has risen over the years. The administration of exogenous virilizing hormones is considered medically necessary for many transgender female to male individuals. Many transgender men seek therapy for virilization, and the mainstay treatment is exogenous testosterone. Transgender women desire suppression of androgenic effects and often use anti-androgen therapy with feminizing exogenous estrogens.

Both the World Professional Association for Transgender Health (WPATH) and the Endocrine Society have created transgender-specific guidelines to help serve as a framework for providers caring for gender minority patients (see, Coleman, E., et al., (2022). Standards of Care for the Health of Transgender and Gender Diverse People, Version 8. International Journal of Transgender Health, 23(S1), S1-S260, available at the wpath.org website). These standards of care are designed to provide clinical guidance for health professionals to assist transsexual, transgender, and gender nonconforming people with safe and effective pathways to achieving lasting personal comfort with their gendered selves, in order to maximize their overall health, psychological well-being, and self-fulfillment.

In accordance with the aspects and embodiments described herein, an individual patient may be identified as being in need of therapy and/or treatment by any currently recognized methodology. For example, the World Professional Association for Transgender Health (WPATH) and the Endocrine Society have created transgender-specific guidelines to help serve as a framework for providers caring for gender minority patients. WPATH recommends that hormone therapy should be initiated once psychosocial assessment has been completed, the patient has been determined to be an appropriate candidate for therapy, and informed consent reviewing the risks and benefits of starting therapy has been obtained. Per WPATH, a referral is required by a qualified mental health professional, unless the prescribing provider is qualified in this type of assessment.

The criteria for therapy include: (I) persistent well-documented gender dysphoria (a condition of feeling one's emotional and psychological identity as male or female to be opposite to one's biological sex) diagnosed by a mental health professional well versed in the field; (II) capacity to make a fully informed decision and to consent for treatment; (III) age of majority; and (IV) good control of significant medical and/or mental comorbid conditions. The fourth criterion can sometimes be the most challenging to interpret. Many patients may have concurrent mood disorders related to their gender dysphoria, and experienced providers may have success alleviating the severity of these symptoms by allowing the patient to begin the medical transition process. Quality of life and perception of personal well-being are important factors and should be considered when patients are being evaluated for hormone therapy initiation. Patients with comorbid psychiatric conditions should be closely monitored and mental health support remains paramount for these patients.

In some aspects and embodiments, the compositions and formulations comprising 5 Alpha-DHT described herein can be based off of, or derived from, current known and developed formulations that comprise testosterone or 5 Alpha-DHT. Such formulations and the therapeutic use and monitoring thereof are generally known to those of skill in the art.

In some aspects and embodiments described herein, the use of 5 Alpha-DHT, optionally in combination with other medicines, hormones and compounds, can provide the benefits of 5 Alpha-DHT hormone therapy and which are not achieved by the use of testosterone (T), and formulations of T (including testosterone undeconoate) when used alone as a testosterone monotherapy. In such embodiments, the compositions and methods can increase the efficacy of an existing method and/or therapy comprising testosterone as a monotherapy.

In some aspects and embodiments the disclosure relates to a method of treatment and/or use comprising 5 Alpha-DHT for affirming gender aesthetics. In some embodiments the disclosure relates to a method of treatment and/or use comprising 5 Alpha-DHT to promote hair growth. In some embodiments the hair growth comprises beard, mustache, chest hair and body terminal hair growth. In particular embodiments, the methods can be used to treat an individual who is or identifies as transgender or transsexual males or as non-binary, and who desire to grow terminal hair in areas of the beard, moustache, chest, pubic or other areas of terminal hair growth that may be recognized or considered as an area of traditional healthy XY human males hair growth (e.g., in postpubertal adult human adult men).

In embodiments, the disclosure provides 5 Alpha-DHT hormone benefits individuals who are or identify as LGBTI+ and non-binary people. In embodiments, the benefit can comprise one or more of improved mental health status, mood, happiness, and/or energy level, and the like.

In embodiments, the disclosure provides 5 Alpha-DHT compositions and related methods that may provide a lifesaving benefit as a part of a gender affirming healthcare treatment under the care of licensed physicians and sexual medicine experts who care for member of the LGBTQI+ and non-binary populations around the world. In embodiments, the formulation compositions and methods may help to decrease the number of suicides that occur in human beings undergoing gender affirming health care and/or mental health care treatments.

In embodiments, the disclosure comprises compositions and related methods that can comprise 5 Alpha-DHT, used alone or in conjunction, or concurrently with other androgens, including but not limited to formulations of testosterone, testosterone undeconoate, 5 Alpha-DHT undeconoate, other androgen formulations, other medicines, and other medical and surgical therapies.

The androgen, 5 Alpha-DHT (commonly referred to as "DHT") is a naturally occurring androgen hormone in human beings. It is present in both human males and females during their development as they develop in their mother's uterus. 5 Alpha-DHT plays a critical role in the development of human beings in utero with regard to health.

In embodiments, the disclosure provides for the use of 5 Alpha-DHT alone, or in combination and/or concurrent use with other formulations comprising hormones including, for example, testosterone therapy and inhibitors of 5 alpha reductase enzymes. The serum and tissue levels of 5 Alpha-DHT are important to have optimized levels in the bloodstream, the serum of the blood, in the central nervous system and in various tissues and organs of the body, including but not limited to the skin, the hair follicles of the body. 5 Alpha-DHT, used alone or in combination and concurrently used formulation of hormones, including testosterone therapy, and other hormones as well as inhibitors of hormone production in the body. One reason for this is that genetic Karyotype (XX) of human females noted to be female at birth who have two X chromosomes in their genetic makeup (Karyotype), will have the potential for variable expression of one of the X chromosomes that they are born with and this is important as many genes are located on the X chromosome, including genes for the Androgen Receptors, (ARs) in the body of human females who are XX genetic females at birth and following birth for the duration of their lives. It is known that there are well over 100 polymorphisms for ARs in human beings and this becomes a more complex problem or issue to consider with regard to "female to male" transgender human males and for transsexual human males.

In accordance with the embodiments disclosed herein, the compositions and methods that can induce 5 Alpha-DHT androgen hormone in central nervous system to levels that can increase mental alertness, mood, and overall brain function in a patient undergoing treatment.

In accordance with the embodiments disclosed herein, the compositions and methods that can promote bone health, prevent osteoporosis, and/or treat osteoporosis or osteopenia in a patient undergoing treatment.

In accordance with the embodiments disclosed herein, the compositions and methods can provide benefits to endocrine health and improve or optimize serum level of important androgens and other hormones in a patient undergoing treatment.

In accordance with the embodiments disclosed herein, the compositions and methods can provide benefits to cardiovascular health and improve or optimize serum level of important androgens and other hormones in a patient undergoing treatment.

In accordance with the embodiments disclosed herein, the compositions and methods can provide for the prevention and/or treatment of gender related issues of any kind, illness, medical illness, mental distress, mental health disorders, and disease, and which are responsive to administration of an amount of 5 Alpha-DHT. The compositions and methods disclosed herein can be used alone, or in fixed combination, with other medicines, hormones, hormone analogues, genetic therapies, and/or surgical procedures, health supplements, and/or genomic and nanotechnology therapeutics and formulations, using multiple drug delivery routes of administration, for the promotion of health and mental health for the promotion of health, mental health and gender affirming health care of LGBTQI+) humans, of any age, including but not limited to those people who are genetically XX females whose gender identity is male, intersex (part male and part female), asexual, unclear, variable, and/or neutral who seek gender affirming healthcare services for transgender, transsexual, and intersex health care and gender affirming healthcare from a wide range of health professionals, physicians, nurses, mental health experts and other experts in LGBTQI+, non-binary, and also transgender health care and mental health care.

Klinefelter Syndrome (47, XXY)

Some people with Klinefelter syndrome are transgender (trans) individuals, including those with a binary and/or non-binary gender identity, represent a growing population with unique healthcare needs. Some trans individuals experience gender dysphoria, which refers to the distress that arises from incongruence between one's gender identity and their sex assigned at birth. A complex set of factors determine one's gender identity, and there has been increasing research into the potential genetic basis of gender incongruence. To date, variations in the oestrogen receptor, oestrogen receptor coactivators, and androgen receptor have been reported in trans individuals. Past studies have also suggested a higher prevalence of Klinefelter syndrome amongst trans individuals presumed male at birth compared to the expected prevalence in the general population.

Klinefelter syndrome (47, XXY) is the most common sex chromosomal disorder in individuals presumed male at birth, affecting 0.02%-0.22% of the population. Klinefelter syndrome is a significantly underdiagnosed condition with estimates suggesting only 25%-50% of individuals are diagnosed. Diagnosis is frequently made in adulthood during fertility assessment. Individuals with Klinefelter syndrome have a primary testicular failure, with resultant clinical features including small testes, gynecomastia, sparse male-pattern body hair and eunuchoid proportions.

While observational studies have suggested a higher prevalence of Klinefelter syndrome amongst trans individuals presumed male at birth relative to rates in the general population, the link between the conditions remains unclear. Existing literature alludes to a twofold explanation behind the predisposition to gender incongruence. Firstly, a fetus with Klinefelter syndrome is exposed to less androgens, which could contribute to a different development of gender identity. Secondly, typical features of Klinefelter syndrome such as gynecomastia and sparse body hair can be perceived as feminine. Some have suggested this may make the individual more vulnerable to doubts surrounding their masculine identity. This aligns with findings in two case reports where gender incongruence improved after testosterone treatment. However, this finding remains dependent on the individual and is subject to speculation.

Another consideration is the prevalence of gender incongruence amongst individuals with Klinefelter syndrome.

One previous analysis examined the Gender Identity/Gender Dysphoria Questionnaire for Adults and Adolescents (GIDYQ-AA) in 46 individuals with Klinefelter syndrome, compared to 43 eugonadal cisgender male controls.

Although individuals with Klinefelter syndrome had lower GIDYQ-AA scores (indicating higher gender dysphoria) than the control group, no individual met the GIDYQ-AA cut-off of <3 for gender dysphoria, nor did any individual meet DSM-V criteria for gender dysphoria. Similarly, there was a significant difference in scores between the individuals with Klinefelter syndrome and a group of transgender women.

Overall, it is important that gender-affirming treatment is appropriately modified according to the risks and medical implications of Klinefelter syndrome. Furthermore, trans individuals should be informed and counselled about the unique risks and different options for feminizing gender-affirming hormone therapy before initiation of treatment.

Androgen Hormones

Testosterone, 5α-dihydrotestosterone and 5β-dihydrotestosterone are steroid hormones and part of the androgen steroid hormone family of hormones. Hormone chemistry and physiology in humans is complex with many pathways of formation and metabolism.

A steroid (or steroid hormone) is a biologically active organic compound with a chemical structure composed of four (4) rings arranged in 3 dimensional stereoisomer specific molecular configurations. Steroids have many important biological functions and effects on physiology including, but not limited to, important components of cell membranes which alter membrane fluidity; and as signaling molecules. Hundreds of steroids are found in plants, animals and fungi. All steroids are produced and manufactured in cells from the sterols lanosterol (opisthokonts) or cycloartenol (plants). Lanosterol and cycloartenol are derived from the cyclization of the triterpene squalene.

The steroid core structure is typically composed of seventeen (17) carbon atoms, bonded in four (4) "fused" rings: three (3) six-member cyclohexane rings (rings A, B and C in the first illustration) and one (1) five-member cyclopentane ring (the D ring). Steroids vary by the functional groups attached to this four-ring core and by the oxidation state of the rings. Sterols are forms of steroids with a hydroxy group at position three and a skeleton derived from cholestane. Steroids can also be more radically modified, such as by changes to the ring structure, for example, cutting one of the rings. Cutting Ring B produces secosteroids one of which is vitamin D3.

It is known that A:B Ring Fusion in the dihydrotestosterone isomer molecules (alpha or beta isomers) may be cis to trans. When the A:B ring fusion is trans (as in 5α-DHT), then the A ring and the B ring are more planer (flat) compared to the acute angulation with the A:B ring fusions in 5β-DHT that is cis. Five alpha reduction of testosterone (T) leads to the more planer (flat) 5α-DHT isomer that is a very potent androgen with the strongest binding kinetics of any naturally occurring, endogenously produced androgen hormone in humans, mammals and animals. The trans-isomer of DHT is the easiest to describe because the fusion of the A & B rings creates a rigid, roughly planar, structure made up of two chair conformations.

In stark contrast, the five beta reduction of testosterone (T) leads to the more angular 5β-DHT isomer at the A:B Ring junction, and 5β-DHT isomer is a very weak androgen with very minimal binding kinetics to the androgen receptor (AR) compared to testosterone (T) and 5α-DHT (naturally occurring, endogenously produced androgen hormones in humans, mammals and animals).

The major synthetic pathway of 5α-DHT formation and metabolism is that testosterone (T) is synthesized in men by the testis and in women either directly by the adrenals and ovaries, or by peripheral conversion of androstenedione. Testosterone is then irreversibly converted to 5α-DHT by the NADPH-dependent enzyme 5α reductase, or aromatized to the potent oestrogen 17β-oestradiol.

The major synthetic pathway of 5β-DHT formation and metabolism is that testosterone (T) is synthesized in men by the testis and in women either directly by the adrenals and ovaries, or by peripheral conversion of androstenedione. Testosterone is then irreversibly converted to 5β-DHT by the NADPH-dependent enzyme 5β-reductase, or aromatized to the potent oestrogen 17β-oestradiol.

Steroid Hormones

The Tetracyclic Chemistry Ring Structure Common to Steroid Hormones There are four rings in a steroid skeleton and hence there are three fusion points. A/B, B/C and C/D rings share two carbons each (fusion). Every fusion center can either be cis- or trans-fused.

The accepted chemistry and pharmacology for numbering of each position of the 4 ring, steroid ring structure essentially follows a uniform pattern except for the methyls, whereas A/B rings have carbon 19, C/D rings have carbon 18. Cholesterol is an important member of the cholestane series of steroids.

Steroids are widely distributed in animals, where they are associated with a number of physiological processes. The generic steroid structure has seven chiral stereocenters (carbons 5, 8, 9, 10, 13, 14 & 17), which means that it may have as many as 128 stereoisomers. With the exception of C-5, natural steroids generally have a single common configuration. The important class of lipids called steroids are actually metabolic derivatives of terpenes, but they are customarily treated as a separate group.

Steroids may be recognized by their tetracyclic skeleton, consisting of three (3) fused six-membered rings and one (1) five-membered ring, as shown below. The four rings are designated A, B, C & D as noted, and the peculiar numbering of the ring carbon atoms (shown in red) is the result of an earlier misassignment of the structure.

The substituents that are attached to the core steroid four ring structure are designated by R are often alkyl groups, but may also have functionality. The R group at the A:B ring fusion is most commonly methyl or hydrogen, that at the C:D fusion is usually methyl.

The substituent at C-17 varies considerably, and is usually larger than methyl if it is not a functional group. The most common locations of functional groups are C-3, C-4, C-7, C-11, C-12 & C-17. Ring A is sometimes aromatic. Since a number of tetracyclic triterpenes also have this tetracyclic structure, it cannot be considered a unique identifier.

The stereochemical conformation of a steroid, may be illustrated using an adequate wedge-and-broken line structure, in addition, steroid hormone chemistry illustrations and determine whether the ring substituents in such a compound occupy axial or equatorial positions.

5 Alpha Dihydrotestosterone (5α-dihydrotestosterone, 5α-DHT)

Some experts in medicine, endocrinology and pharmacology have referred to 5 Alpha Dihydrotestosterone (5α-dihydrotestosterone, 5α-DHT and DHT) as a prostate sparring androgen compared to testosterone. (See, Swerdloff R S, et al., *Dihydrotestosterone: Biochemistry, Physiology, and Clinical Implications of Elevated Blood Levels*. Endocr Rev. 2017 Jun. 1; 38(3):220-254).

5 Alpha Dihydrotestosterone (5 Alpha-DHT, 5α-dihydrotestosterone, 5 Alpha-DHT, 5α-DHT, androstanolone or stanolone) is an endogenously produced androgen sex steroid hormone in humans, mammals and animals. The enzyme 5α-reductase catalyzes the formation of 5α-DHT from testosterone in certain tissues that have both the proper genetics and epigenetics that regulate the cell biology and molecular biology of individual cells that make up tissues, organs and well described tissues that make up organ systems, including (but not limited to) the prostate gland, seminal vesicles, epididymides, skin, hair follicles, liver, and brain. This enzyme mediates reduction of the C4-5 double bond of testosterone and in so doing metabolized testosterone into 5α-dihydrotestosterone (5α-DHT).

Relative to testosterone (T), 5α-DHT is considerably more potent as an agonist of the androgen receptor (AR), and this is related to the binding affinity of the 5α-DHT and 5α-DHT dimer complexes to the AR as well as the longer 5α-DHT receptor binding kinetics and duration of binding to the AR as compared to testosterone (T).

In addition to its role as a naturally produced hormone in humans, mammals and animals, topical pharmaceutical formulations of 5α-DHT has been used as a medication in countries that include France and Belgium since the early 1980's, for instance in the treatment of adult men with gynecomastia or male hypogonadism (below normal serum testosterone levels in men who often have symptoms recognized by physicians as related to below normal or low normal levels of total serum testosterone or free serum testosterone. A topical formulation of 5α-DHT is sold by Besins Healthcare and marketed under the brand name, Andractim® 2.5%5α-DHT Gel. The Besins Healthcare company has created a formulation of 5α-DHT that is a 0.7% 5α-DHT Gel. The Besins Healthcare Company, or prior companies owned by the Besins Family over the past 50 years have sponsored research and research partnerships with companies including Unimed Pharmaceuticals of Buffalo Grove, IL in the 1990's and early 2000's years. Such clinical trials and studies have assessed the clinical use of 5α-DHT topical hydroalcoholic gel formulations in the treatment of HIV Associated Muscle Wasting Disorders in the U.S. and perhaps outside the U.S. in the 1990's, and also assessed the use of 5α-DHT topical hydroalcoholic gel formulations in the treatment of cancer cachexia wasting disorders in the U.S. and perhaps other countries in the 1990's. Additional studies of 5α-DHT topical hydroalcoholic gel formulations have been clinical studies in the U.S. with regard to changes of prostate health status in multicenter studies in the U.S. In addition, excellent studies have been performed in the U.S. comparing 5α-DHT topical hydroalcoholic gel formulations of 2.5% v. 0.7% to placebo in human clinical studies assessing pharmacokinetics at the Harbor UCLA Medical Center. This research has been published in the medical literature and is most useful.

5α-DHT is biologically important for sexual differentiation of the male genitalia during embryogenesis, maturation of the penis and scrotum at puberty, growth of facial, body, and pubic hair, and development and maintenance of the prostate gland and seminal vesicles. 5α-DHT is produced from the less potent testosterone by the enzyme 5α-reductase in select tissues, and is the primary androgen in the genitals, prostate gland, seminal vesicles, skin, and hair follicles. 5α-DHT signals mainly in an intracrine and paracrine manner in the tissues in which it is produced, playing only a minor role, if any, as a circulating endocrine hormone. Circulating serum levels of 5α-DHT are ¹/₁₀th and ¹/₂₀th those of testosterone in terms of total and free concentrations, respectively, [6] whereas local 5α-DHT levels may be up to 10 times those of testosterone in tissues with high 5α-reductase expression such as the prostate gland. In addition, unlike testosterone, 5α-DHT is inactivated by 3α-hydroxysteroid dehydrogenase (3α-HSD) into the very weak androgen 3α-androstanediol in various tissues such as muscle, adipose, and liver among others, and in relation to this, 5α-DHT has been reported to be a very poor anabolic agent in muscle tissues when administered exogenously as a medication because is it rapidly metabolized in muscle tissue.

Androgens and Hair Growth and Hair Loss

There is little understanding at a genetic or epigenetic level as to what key mechanisms and molecular biology regulate vellus hair follicle cycles. This is true for both scalp hair growth, scalp hair alopecia, and a host of other aspects of scalp hair biology and scalp hair follicle individual behavior over the human lifespan. This is also true for facial hair growth in both human males and females from childhood to puberty/adolescence, early adulthood, middle age and older ages.

The hair cycle and the interaction of a host of complex factors that relate to the genetics, epigenetics, endocrine, intracrine and a host of other factors is not well understood with regard to human hair growth on the scalp or of the face or the human body of males and females. It is not known why some vellus hair follicles transform to terminal hair follicles in any precise way for human hair biology in human males and females.

There are some general thoughts by physician and scientific experts in the genetics and epigenetics or hair biology about the key role of genetics and epigenetics and how dermal papilla cells in vellus and terminal hair follicles may or may not respond to endogenous levels of circulating androgens and other hormones. It is clear that 5 Alpha-DHT is not the sole cause of scalp alopecia in humans and that genetics and epigenetics play a key and highly individual role in human hair growth, human hair traits, and human hair alopecia disorders.

The role of the use of androgens in transgender populations, particularly "female to male transgender males" who have at birth a XX genetic Karyotype, is more complex and is not well understood. While testosterone is the mainstay androgen for use by experts in medicine and transgender care of transgender male humans, the impact of exogenous use of testosterone hormones and other therapies at the hair follicle level of the scalp, facial areas, the beard, mustache, chest and other areas is less well known.

The applicant is not aware of 5 Alpha-DHT use in the treatment of female to male transgender people. The applicant's present invention discloses a novel, nonobvious and useful therapy for use by healthcare experts in the area of transgender gender affirming pharmaceutical therapeutics using 5 Alpha-DHT, alone in in combination with other medicine, hormones and compounds.

In addition to well recognized and accepted important biological functions in humans, mammals and animals, 5α-DHT also plays an important causative role in a number of androgen-dependent conditions including hair disorders and conditions like hirsutism excessive facial/body hair growth) in human females with a XX Karyotype, Metabolites of 5α-DHT have been found to act as neurosteroids with their own AR independent biological activity. 3α-Androstanediol is a potent positive allosteric modulator of the GABAA receptor, while 3β-androstanediol is a potent and selective agonist of the estrogen receptor (ER) subtype ERβ. These metabolites may play important roles in the central effects of 5α-DHT and by extension testosterone, including their antidepressant, anxiolytic, rewarding/hedonic, anti-stress, and pro-cognitive effects.

In some aspects, the disclosure provides compositions, (including pharmaceutical formulations), methods, and uses for androgen-related therapy comprising 5 Alpha Dihydrotestosterone, and salts, esters, fatty acid esters, and prodrugs thereof. Such formulations comprising 5 Alpha-DHT, for example, 5 Alpha-DHT Undeconoate can be useful when administered as an oral therapy, an injection therapy, and when used as a topical therapy in a subject who is in need of, or desirous of, methods for gender affirming health care medical and mental health needs, including supplemental and/or supportive methods associated with gender affirmation, general wellness, and mental health.

In some embodiments, methods can comprise administration (e.g., injection or oral administration) of 5 Alpha-DHT in forms that are commonly associated with various testosterone formulations (e.g., as 5 Alpha-DHT undecanoate, 5 Alpha-DHT enanthate, 5 Alpha-DHT cypionate, and 5 Alpha-DHT propionate) as are generally known in the art and which may be commercially available.

Masculinizing Hormonal Therapy

Masculinizing hormone therapy commonly relies on testosterone to inhibit estrogen and exert robust masculinizing effects. Testosterone has a significant effect on both facial hair growth and body hair growth, which has been reported previously (e.g., Motosko et al.). Masculinizing hormone therapy is associated with an increased risk of androgenic alopecia, which is often an undesirable side effect. Treatment with 5-α-reductase inhibitors such as finasteride and dutasteride have been used to reduce this side effect and may be used to treat hair loss in this population, as they decrease dihydrotestosterone—the primary androgen involved in the pathogenesis of androgenetic alopecia—without decreasing testosterone levels.

It is generally accepted that 5 Alpha-DHT (5α-DHT) is not converted or metabolized back to testosterone. Nor is it metabolized to estradiol by the enzyme aromatase. It is generally accepted that 5 Alpha-DHT is not converted or metabolized back to testosterone. Nor is it metabolized to estradiol by the enzyme aromatase.

The term "DHT" can be used herein when referring to 5α-DHT. The enzyme 5α-reductase catalyzes the formation of DHT from testosterone in certain tissues including the prostate gland, seminal vesicles, epididymides, skin, hair follicles, liver, and brain. This enzyme mediates reduction of the C4-5 double bond of testosterone. Relative to testosterone, 5α-DHT is considerably more potent as an agonist of the androgen receptor (AR).

In addition to its role as a natural hormone, 5α-DHT has been used as a medication, for instance in the treatment of low testosterone levels in men. While a great deal of chemistry, pharmacology, pharmacokinetics, and clinical pharmacology is known and in the literature for 5α-DHT, there is very little data published or available for healthy human beings, healthy mammals and animals on seemingly basic chemistry, pharmacology, pharmacokinetics, normal ranges of 5β-DHT in humans during embryogenesis, during infancy, during childhood, during puberty, during adolescence, during young adulthood, middle age adult years, the older age groups of over 50, over 60, over 70, over 80 y.o. in men and women, mammals or animals in healthy human males and females, mammals or animals.

In 2017, a most review paper was published by Swerdloff R, et al and was a paper that is cited as: Swerdloff R S, Dudley R E, Page S T, Wang C, Salameh W A. Dihydrotestosterone: Biochemistry, Physiology, and Clinical Implications of Elevated Blood Levels. Endocr Rev. 2017 Jun. 1; 38(3):220-254. doi: 10.1210/er.2016-1067. PMID: 28472278; PMCID: PMC6459338. The paper noted above, that will be referred to as Swerdloff R S, et al 2017, was a paper titled: "Dihydrotestosterone: Biochemistry, Physiology, and Clinical Implications of Elevated Blood Levels."

The Swerdloff R S, et al 2017 paper shows a common approach and convention used by the medical and scientific community to refer to 5 Alpha Dihydrotestosterone (5α-DHT) as just "DHT". While common, and while in common use, even in the patent art, it is generally accepted by physicians, scientists and even the general public that the letters "DHT" when used in medical papers, and scientific papers and even publications or media formats of communication including Internet publications and digital and electronic forms of communication is referring to 5 Alpha Dihydrotestosterone (5α-DHT).

While the common approach and convention is well established in the medical and scientific communities is to simply abbreviate "dihydrotestosterone" into the letters DHT, it is helpful for the purposes of this patent application to make a clear distinction between what is more precisely terms "5 Alpha Dihydrotestosterone" (5α-DHT) and the 5 Beta Reduced metabolite of testosterone (T) that is precisely described as 5 Beta Dihydrotestosterone (5β-DHT).

The Swerdloff R S, et al 2017 paper notes the following: "DHT is the 5α-reduced metabolite of testosterone (T) that is principally converted from T in target organs such as prostate, skin, and liver. Synthesis can also occur from other precursors, but these pathways, although potentially important in some tissues (e.g., in prostate), are minor. Intracellular DHT is a more potent androgenic agonist than T, and its presence in some tissues such as the prostate is necessary for the full organ development and function. Circulating DHT levels are of much less importance than T for optimizing the intracellular DHT concentrations due to the presence of a rate-limiting enzyme, 5α-reductase (SRD5A; types I and II)."

"The clinical benefits associated with lowered serum DHT levels after 5AR inhibitor therapies appear to have led to the misconception that circulating DHT is an important stimulus for androgenic action in the prostate gland. However, studies in which serum DHT concentrations were markedly elevated by exogenous administration of DHT had almost no effect on prostate DHT concentrations, prostate size, and lower urinary tract symptoms (see "Intraprostatic Control Of DHT in the Presence of Fluctuating Levels of Circulating Androgens" and associated references). The reason for this highlights fundamentally important control mechanisms in androgen target tissues that finely regulate pathways for androgen synthesis and degradation to maintain DHT homeostasis.

These intracellular processes do not appear to be affected by circulating DHT concentrations. Furthermore, it is well documented that DHT can be synthesized in androgen-sensitive tissues such as prostate from substrates other than T (e.g., from 17-hydroxypregnenolone and 17-hydroxyprogesterone in what is termed the "backdoor" pathway and from 5α-androstane-3α,17-β-diol via the intracrine reverse synthesis pathway) (4). We will also explore the implications of modest increases in serum DHT that are seen with T replacement therapy (TRT; including, for completeness, DHT preparations) for male hypogonadism and discuss why these likely have minimal clinical implications for men treated with androgens. Serum DHT levels are dependent upon the concentration of serum T achieved with TRT and the expression of normal levels of functional SRD5A in tissues. In adult eugonadal men, serum DHT levels are about one-tenth that of total serum T concentrations.

The molecular formula of 5 Alpha-DHT is: Molecular Formula $C_{19}H_{30}O_2$. The molecular weight of 5 Alpha-DHT is 290.4 g/mol. The preferred IUPAC name for 5 Alpha-DHT is: 1S,3aS,3bR,5aS,9aS,9bS,11aS)-1-Hydroxy-9a,11a-dimethylhexadecahydro-7H-cyclopenta[a]phenanthren-7-one.

Drug Delivery Options

In various aspects relating to the methods provided herein, any known and available routes of administration and delivery (i.e., therapeutic and/or cosmetic) for 5 Alpha-DHT may be used. In some non-limiting embodiments, administration can comprise:

1. Topical application of liquid, gel, lotions, hydroalcoholic gels, creams, pellets, sprays and any variety of topical formulations of DHT, including nanotechnology formulations that are appropriate for application to the skin, the mucosal surfaces of the nose and/or nasopharynx, the mucosal surfaces of the of the mouth, sublingual application and topical application to areas of the body including the skin of the body, face, pubic region, and/or genitalia.
2. Injectable administration such as intramuscular injections, intraperitoneal, subcutaneous injections, intradermal or intravenous delivery, among others. In addition, for the administration of DHT formulations via injections that may be a depot delivery of administered DHT formulations, including formulations of DHT Undeconoate formulations, and/or other formulations of DHT.
3. Oral delivery of DHT formulations including, for example, as liquids, tinctures, tablets, pills, solutions, capsules, pellets, buccal films, and the like which may be swallowed and enter the gastrointestinal system, or which may be absorbed systemically through oral mucosa.
4. Topical sprays of liquid aerosolized formulations of DHT to the nasal or oral mucosa and the nasopharynx for provide for transmucosal drug delivery to the systemic circulation.
5. Topical application of liquid, gel, lotions, hydroalcoholic gels, creams, and a variety of formulations of DHT, including nanotechnology formulations, which are applied to areas of the skin and then followed by the use of micro derm roller type apparatus with small diameter micro needles used to facilitate transepidermal and transdermal topical drug delivery.
6. Sublingual pellets, films, or tablets designed for transmucosal drug delivery to the systemic circulation.
7. Intradermal insertion/placement of formulations, such as depot or extended release formulations (e.g., pelletized formulations).

Formulations

In accordance with the aspects and embodiments disclosed herein, the formulations used in connection with the methods and uses disclosed herein can comprise 5 Alpha-DHT as a composition that is appropriate for therapeutic applications. In some embodiments, the formulations can comprise a formulation that is known and/or commercialized for testosterone. In some embodiments, the formulations can include the non-limiting examples of:

1. Topical formulations of 5 Alpha-DHT that are hydroalcoholic gel formulations with a concentration range from 0.00001% DHT up to 50% DHT. Such formulations may be made for clinical use by compounding pharmacists and pharmacies. Topical DHT formulations may be of 2.5% DHT USP hydroalcoholic gels, 0.7% DHT USP hydroalcoholic gels, and may also be made of a variety of strengths including 0.05% DHT formulations, 0.10% DHT formulations, 1.0% formulations and formulations that are between 0.00001% DHT up to 50% DHT hydroalcoholic gels. Such formulations may include penetration enhancement chemicals that may enhance transdermal and transepidermal drug delivery, such as isopropyl myristate.
2. Composition that can comprise one or more solvents. Typically, the solvent comprises a non-aqueous solvent (or mixed aqueous/non-aqueous solvent) that is capable of dissolving and/or suspending DHT, optionally in combination with one or more absorption promoter. In some embodiments the solvent comprises a low boiling point, i.e., less than 100° C. at atmospheric pressure, so that it can evaporate rapidly on contact with the skin. Such solvents may be selected from the non-limiting examples of volatile compounds such as ethanol, isopropanol or ethyl acetate; preferably ethanol and/or isopropanol, or combinations thereof. In some embodiments, ethanol is a preferred solvent. Ethanol contributes with efficiency towards the transcutaneous passage of the active principle by evaporating rapidly on contact with the skin and by allowing a local saturation of DHT, which favors percutaneous diffusion from the vehicle to the epidermis and the dermis. The absolute ethanol content is from about 50% to about 75%, preferably from about 60% to about 70%, more preferably from about 63 to about 67% and most preferably of about 66%, these percentages being expressed by weight relative to 100 g of formulation. The pharmaceutical composition, in some embodiments, may also comprise an aqueous vehicle. The aqueous vehicle makes it possible to dissolve the hydrophilic molecules contained in the formulation and can also promote the diffusion of the lipophilic molecules of the formulation towards the horny layer. It may also act as a pH regulator. The aqueous vehicle may be a selected buffer or may simply be purified water. The aqueous vehicle can comprise a content of between about 15% to about 45%, preferably from about 20% to about 40%, more preferably from about 25 to about 35% and most preferably of about 27%, these percentages being expressed by weight relative to 100 g of formulation. The aqueous vehicle content can be adjusted during the manufacturing process in order to reach the weight of 100 g for 100 g of the composition. According to some exemplary embodiments, purified water is the preferred aqueous vehicle used in the composition.

The pharmaceutical composition according to some exemplary embodiments may further comprise a gelling agent. Advantageously, and depending on the type of gelling agent used, the composition comprises from about 0.2% to about 2% of a gelling agent, preferably from about 0.3% to about 1%, more preferably from about 0.4% to about 0.8%, and most preferably of about 0.5%, these percentages being expressed on a weight basis per 100 g of the pharmaceutical composition.

The gelling agent is preferably selected from the non-limiting examples of carbomers and cellulose derivatives. According to some exemplary embodiments, the gelling agents may be selected from the following compounds: Carbomers or polyacrylic acids such as carbopol 980 or 940 NF, 981 or 941 NF, 1382 or 1382 NF, 5984, 2984 or 934 NF, Pemulen TR1 NF or TR2 NF, Ultrez, Synthalen CR, and the like: Cellulose derivatives such as ethyl cellulose, hydroxypropyl cellulose, hydroxyethyl cellulose, hydroxypropyl methyl cellulose (HPMC), carboxymethyl cellulose (CMC), and the like.

These gelling agents make it possible to increase the viscosity of the formulations according to some exemplary embodiments, but may also act as solubilizing agents. Hydroxypropylcellulose and Carbopol® 980 (carboxyvinyl polymer grade 980, polymerized in an ethyl acetate/cyclohexane system) are preferred in the context of some exemplary embodiments of the disclosure.

NONLIMITING EXAMPLES OF 5 ALPHA-DHT FORMULATIONS

The following formulations illustrate some non-limiting and exemplary embodiments of the compositions that can be used in connection with the methods and uses contemplated herein.

Example Formulation 1

Topical formulations of topical DHT may include formulations that are composed of the following components, where the amounts are given per 100 g of gel:

Dihydrotestosterone 0.7 g
Ethanol 95 71.0 g
Carbopol® 980 0.5 g.
Isopropyl myristate 0.7 g
Triethanolamine 0.5 g.
Purified water qs 100.0 g

Example Formulation 2

Topical formulations of topical DHT may include formulations that are composed of the following components, where the amounts are given per 100 g of gel:

Dihydrotestosterone 2.5 g
Ethanol 95 71.0 g
Carbopol. 980 0.5 g.
Isopropyl myristate 0.7 g
Triethanolamine 0.5 g.
Purified water qs 100.0 g

Example Formulation 3

Topical formulations of topical DHT may include formulations that are composed of the following components, where the amounts are given per 100 g of gel:

Dihydrotestosterone 0.0001 g to 50 g
Ethanol 95 71.0 g
Carbopol. 980 0.5 g.
Isopropyl myristate 0.7 g
Triethanolamine 0.5 g.
Purified water qs 100.0 g

Example Formulation 4

Oral formulation of 5 Alpha-DHT Decanoate capsules.

Oral formulations of DHT, including DHT Undeconoate may include dihydrotestosterone undeconoate capsules for oral use. Capsules may be in the following strengths: 158 mg, 198 mg, 237 mg per capsule and administered as directed by the prescribing physician. Formulations may be taken with food or not with food or drink based on the prescribing physician's orders.

Example Formulation 5

Topical formulation of 5 Alpha-DHT in a liquid, lotion or cream made up by a compounding pharmacist that is of the 0.00001% to 50% concentration strength of DHT. This may include lotions such as Vanicream lotions that are readily available to U.S. pharmacies. Topical formulations of DHT may be administered and applied to the skin of the abdomen, legs, back, upper arms, shoulder, axilla, face, beard areas and pubic hair skin regions. Topical formulations of a 2.5% DHT hydroalcoholic gel formulation may be dosed and prescribed by a licensed physician with the topical administration/application of 5 grams of DHT gel that will contain 125 mg of DHT and also with administration of 10 grams of gel that will contain 250 mg of DHT.

Administration of Formulations to the Skin

The skin is a multifunctional and multicompartment organ affected by diseases and their treatments. The bulk of percutaneous absorption of most agents is through the stratum corneum, which covers the entire skin surface. Of note, hair follicles and hair shafts can also play an important role in absorbing topical medications and compounds applied to the surface of the skin. Epidermal structure and sweat glands are also potential pathways of absorption of topically applied medications or hair growth agents. Hair follicles form a lipid-rich pathway for drug absorption and also represent a special shunt pathway to allow for a direct pathway for topical medications to reach key hair follicle structures and also provides a localized drug reservoir that can enhance local effects of medicines in the hair follicles. The absorption of drugs and chemicals into and onto hair shafts also can be used to measure prior drug exposure.

Some research suggests that there are essentially two types of hair, soft lanugo hair called vellus hair, and a thicker, coarser hair called a terminal hair. Vellus hair is found all over the body except for the palms and soles. Hair growth can be further differentiated as being either androgen dependent or androgen independent growth. This distinction becomes important during puberty and throughout adulthood. Other research notes an intermediate type of hair that is on the continuum between vellus hair and terminal hair. In the medical care, and medical gender supportive/affirming therapies that is provided by health care experts, hair growth on the scalp is not solely dependent on androgen hormones and may be uniquely challenging with regard to the use of both topical and systemic therapies of testosterone (T) and testosterone formulations of any kind (including testosterone undeconoate formulations) and formulations of other androgens and 5 alpha reductase inhibitors.

Hair growth of eyelash hair or eyebrow hair is not androgen dependent. As with scalp hair, young children with normal health are usually able to grow scalp hair, eyelash hair and eyebrow hair before puberty.

Topical Formulations of DHT and the Skin of Humans

In the epidermis, the stratum corneum is the outer layer and is 5-600 microns thick. The stratum corneum is the major barrier to percutaneous absorption of drugs and also helps minimize the loss of water from the body. It is made of "dead" epidermal cells that cannot reproduce and have lost their nuclei and mitochondria. It possesses multiple proteins and lipids that may reversibly or irreversibly bind drugs. Many chemicals and physical treatments to enhance percutaneous absorption work within the stratum corneum. Many drugs may partition into the stratum corneum and can function as a reservoir for drugs that will diffuse into the rest of the skin, even after topical application of the drug has ceased. The stratum corneum varies in thickness. Facial and post auricular have the thinnest stratum corneum.

The living layers of the epidermis with metabolically active cells comprise a layer of ~100 microns thick. The lowest or basal layer of the epidermis is called the stratum basale and is responsible for the bulk of cell division. Several cell layers in the spinous layer (stratum spinosum) contain cells that actively synthesize most epidermal proteins, especially keratins. The uppermost layer of the living epidermis is the stratum granulosum. This layer is where extracellular lipids are extruded from the epidermis.

There is a superficial capillary plexus of blood vessels between the dermis and epidermis that is the site of the majority of the systemic absorption of cutaneous drugs. There are a large number of lymphatics as well in this area.

The dermis is about 1,200 microns thick that is in part composed of collagen and proteoglycans that may bind drugs. Below the dermis, is a subcutaneous tissue called the hypodermis.

The hair shaft is formed by keratinized cells containing highly organized material. Hair has the appearance of an extremely elongated cylinder. The hair shaft has three (3) regions: The cuticle, the cortex and the medulla found close to the center of the hair shaft.

Lanugo hairs, the first body hairs formed in the embryo, are vellus in character, but often longer than the vellus shafts of the adult. The vellus hair shaft is short, thin, fine, lightly pigmented, and with no medulla. A vellus hair follicle is defined as a small follicle that extends no deeper than the upper dermis and produces a shaft no wider than its internal root sheath. Although vellus follicles may lack arrector pili muscles in some areas, vellus hair follicles are associated with these structures on the face. With maturity and exposure to androgens, regional human hair follicles switch in morphology to terminal follicles that produce terminal hair shafts. The inverse terminal-to-vellus switch occurs on the scalp of the genetically susceptible androgenic alopecia individuals after exposure to androgens.

The hair cycle appears to be central to the vellus-to-terminal hair follicle switch because phenomenologically the cycle appears to initiate that process; the follicle must cycle in order for the switch to occur. We do not yet know how the cycle is related to this transformation, although it may be due to a gradual change in the size of the papilla with the completion of each cycle. Relatively little attention has been given to this switch phenomenon mechanistically; in fact, even the follicle that characteristically switches has not yet been fully characterized.

The wide response range of hair to androgens reflects highly variable inherent genetic and highly complex epigenetics of hair follicles (vellus, intermediate and terminal hair follicles) differences of hair depending on body site. There is a graded response of regional hairs to androgen levels; inguinal and axillary follicles, for example, are stimulated to grow under low levels of androgen, and facial hair to high levels, while deep temporal/occipital scalp and eyebrow/eyelash hair are insensitive to androgen levels altogether. This principle underlies the success of scalp hair transplants for male pattern balding, where androgen-insensitive hairs (occipital area) are transplanted to sites of androgen-sensitive hairs (frontal, parietal, coronal areas). Thus, one must distinguish between hairs that are androgen dependent (axilla, mustache, beard and chest), androgen insensitive (eyebrow and eyelash), and androgen independent but androgen sensitive (scalp vertex in susceptible individuals). Ultimately, these interfollicular and interregional differences must stem from the way a given follicle is genetically programmed and how it responds to androgen stimulation, its androgen target genes, and the nature of its androgen receptor-mediated signal transduction events. Unfortunately, these parameters have not yet been dissected.

Hair growth during and after puberty of mature terminal hairs on the face in the mustache and beard areas is androgen dependent and related to genetics and epigenetics in both human males and females. The same is true for terminal hair growth in the chest and other parts of the male body. This process begins in puberty in boy who are developing secondary sex characteristics on their way to becoming young adult men.

Hair biology and hair loss physiology are complex and relate to a wide range of genetic variables, ethnic background, family history & genetics, health status, medication use, diet and even psychosocial stress levels.

The exploration and investigation of possible treatment options for treating scalp alopecia disorders in humans, mammals and animals and promotion hair growth in humans, mammals and animals requires an in depth understanding of hair biology, endocrinology, genetic hair growth variables in both sexes, and hormonal regulation of hair growth factors in different areas of the skin.

Genetics and epigenetics play an important role both in the density and number of hair follicles in the mustache, beard and chest hair areas. In addition, genetics and epigenetics may determine the number of androgen receptors located in individual hair follicle cells on the scalp, face and chest. Further, genetics and epigenetics helps to determine the level and activity of the enzymes 5 alpha reductase 1, 2 and 3 that often play an important role within the body and also in the hair follicle cells relating to the growth of mature terminal facial hair, mustache hair, beard hair, chest hair and other androgen dependent hair growth.

Ethnic origin, and geo ethnic origin, and ancestry can play an important role and have a great impact on the hair growth in men. This is true for body hair, scalp hair, facial hair growth, chest hair growth, scalp hair growth and hair growth on the entire body.

All naturally occurring androgens play a critical role in human health and all androgens have major conversions and important metabolic pathways for interconversion into other hormones, other steroid hormones and other sex hormones. The same is true for animals. It is well known that at the cellular level, testosterone is routinely converted into to 5 Alpha dihydrotestosterone via the enzymes five alpha reductase 1, 2 and 3. This conversion of testosterone to 5 Alpha dihydrotestosterone within hair follicles, that commonly happens within cells (to a variable degree), creates a very powerful anabolic androgenic steroid hormone, 5 Alpha dihydrotestosterone (5 Alpha-DHT), that is 2 to 5 times more potent and powerful than testosterone in causing a wide range of physiologic effects in the body. This is particularly true with regard to androgen dependent hair growth in the human body compared to testosterone. The same is true in mammals and animals.

In aspects, the disclosure provides pharmaceutical formulations, method of use, methods of treatment, and methods of supportive treatment comprising 5 Alpha Dihydrotestosterone (5α-DHT, 5 Alpha-DHT, DHT) alone or in fixed combination, with other, medicines, hormones, or therapies and/or surgery. In particular embodiments, the disclosure provides formulations, methods of use, methods of treatment and methods of supportive treatment for patients in need of, or in patients who wish to pursue, gender affirming hormone therapy. In embodiments, the patients may be, or may identify as, lesbian, gay, bisexual, transgender, queer and intersex (LGBTQI+) and non-binary humans, and may be of any age. In various embodiments, the methods can promote or enhance overall health, mental health, general wellness, aesthetics, hair growth of facial, body and pubic hair.

In some embodiments, the disclosure provides a broad range of formulations comprising 5 Alpha-DHT including, for example, oral, topical, injectable, implantable, transdermal, transfollicular and other recognized drug delivery routes that find use in hormone therapy in humans. The disclosure provides a wide range of dosing options including, for example, daily, weekly, or monthly dosing, all of which are inclusive of interval therapy periods and cycles as generally known in the art. Such dosing regimen comprise administration of 5 Alpha-DHT formulations for a period of time (treatment period) and then may be halted for a period of time (a non-treatment interval) as an intermittent dosing regimen that provides treatment benefits and minimizes side effects, as well as reduces potential transfer to others.

Some aspects and embodiments of the disclosure provide for the use of formulations, compositions, and methods comprising 5 Alpha Dihydrotestosterone (5α-DHT, 5 Alpha-DHT), by any known and/or recognized drug delivery route for other androgen hormones. In embodiments, the formulations and related methods can comprise any drug delivery route, including but not limited to pharmaceutical formulations of oral, injectable, implantable, or topical monotherapies for patients in need of, or in patients who wish to pursue, gender affirming hormone therapy for the promotion of hair growth of facial, body and pubic hair, and who have a genetic or rare diseases including, but not limited to androgen resistance disorders.

In some embodiments, the use can comprise compositions and methods the comprise 5 Alpha-DHT or formulations thereof, and testosterone (T) (example: testosterone undeconoate formulations). Such uses can comprise concurrent administration via any drug delivery route, including but not limited to pharmaceutical formulations of oral, injectable, implantable, or topical monotherapies for the for promotion health, mental health, gender affirming health and healthcare for lesbian, gay, bisexual, transgender, queer and intersex and non-binary (LGBTQI+) humans, of any age, including the promotion of hair growth of facial, body and pubic hair, of any age, and in humans with genetic and rare diseases including, but not limited to androgen resistance disorders.

In various aspects and embodiments compositions in accordance with some example embodiments comprise 5 Alpha-DHT in an amount from 0.00001% to 99.999%. In some embodiments, the 5 Alpha-DHT comprises 5 Alpha-DHT undeconoate. In embodiments, the concentrations of 5 Alpha-DHT or 5 Alpha-DHT undecanoate and may range from about 0.001% to about 50%, measured w/w, /w/v, or v/v. In additional embodiments, the concentration of 5 Alpha-DHT may be from about 0.5% to about 25%; in further additional embodiments, the concentration of 5 Alpha-DHT may be from about 0.5% to about 10%; from about 0.5% to about 5%; or from about 0.5% to about 2%. Concentrations may be measured in weight to weight, weight to volume or volume to volume. In some further embodiments, concentrations of 5 Alpha-DHT or 5 Alpha-DHT undecanoate range from about 0.5% or about 1.0% to about 25% (i.e., 1, 2, 3, 4, 5, 6, 7, 8, 9, 10, 11, 12, 13, 14, 15, 16, 17, 18, 19, 20, 21, 22, 23, 24 or 25%), measured w/w, w/v, or v/v.

In some embodiments, the 5 Alpha-DHT formulations is formulated for topical application so as to be able to be absorbed into the hair follicle structures areas of the skin in humans in a targeted manner. In addition, to allow the formulation to also adsorb onto a hair shaft itself and be drawn by capillary action to the target hair follicle bulb and other hair follicle structures.

Additional useful formulation properties are the ability to cross the surface of the skin and travel to the hair follicle bulb matrix by trans-epidermal diffusion or by transdermal diffusion, following Fickes' laws of diffusion. This is beneficially accomplished by the addition of one or more dermal penetration enhancement agents, such as a lower alcohol, including methanol, ethanol, propanol, or isopropanol.

In one embodiment, the disclosure provides a method for topical administration of 5 Alpha dihydrotestosterone in a liquid, lotion, foam, or gel. The liquid, lotion, foam or gel comprises 5 Alpha dihydrotestosterone (5α-DHT), used alone or in combination with another androgen, which would be applied to the outer surface of skin areas where a person would hope to increase hair growth in the scalp areas. The embodiment may include one or more lower alcohols, such as ethanol or isopropanol, a penetration enhancing agent such as isopropyl myristate; a thickener; and water.

Additionally, the present invention may optionally include salts, emollients, stabilizers, antimicrobials, fragrances, and propellants.

In another embodiment, the disclosure provides a method for topical administration of 5 Alpha dihydrotestosterone in a lotion. The lotion comprises 5 Alpha dihydrotestosterone used alone or in fixed combination with other hair growth medications; including other androgens, bimatoprost, prostamides, prostaglandins, minoxidil or apocrine hair growth factors to promote and enhance hair growth of scalp hair growth in humans, mammals or animals that would be applied to the outer surface of skin areas where a person would hope to increase terminal and intermediate scalp hair growth. The embodiment may include one or more lower alcohols, such as ethanol or isopropanol, a penetration enhancing agent such as isopropyl myristate; a thickener; and water. Additionally, the present invention may optionally include salts, emollients, stabilizers, antimicrobials, fragrances, and propellants.

In other embodiments the disclosure provides a method for topical administration of 5 Alpha dihydrotestosterone in a foam, cream, a gel, an aerosolized spray, foam or other manner for delivering 5 Alpha dihydrotestosterone, used alone or in fixed combination with other hair growth medications; including other androgens, bimatoprost, prostamides, prostaglandins, minoxidil or apocrine hair growth factors to promote and enhance hair growth of scalp hair growth in humans or animals that can be applied to the outer surface of skin areas where a person would hope to increase scalp hair growth.

These embodiments may include one or more lower alcohols, such as ethanol or isopropanol, a penetration enhancing agent such as isopropyl myristate; a thickener; and water. Additionally, the present invention may optionally include salts, emollients, stabilizers, antimicrobials, fragrances, and propellants.

As used herein, the term "lower alcohol," alone or in combination, means a straight-chain or branched-chain alcohol moiety containing one to about six carbon atoms. In one embodiment, the lower alcohol contains one to about 4 carbon atoms, and in another embodiment the lower alcohol contains two to about 3 carbon atoms. Examples of such alcohol moieties include methanol, ethanol, ethanol USP (i.e., 95% v/v), n-propanol, isopropanol, n-butanol, isobutanol, sec-butanol, and tert-butanol. Alcohols can be used in combination with various amounts of water.

In one embodiment, the present disclosure is directed to a method for the topical application of 5 Alpha-DHT for percutaneous administration (transdermal use) applied the skin used alone, or concurrently, or in fixed combination, with other hormones, medicines or pharmaceutical compounds. In some embodiments, the 5 Alpha-DHT can comprise a gel comprising one or more lower alcohols, such as ethanol or isopropanol; a penetration enhancing agent; a thickener; and water. In one embodiment, the gel comprises an anionic polymer thickening agent precursor neutralized with a hydroxide releasing agent, such as, e.g., sodium hydroxide.

Additionally, the formulations and compositions in accordance with the disclosure can optionally include salts, emollients, stabilizers, antimicrobials, fragrances, and propellants.

In embodiments, the disclosure relates to the use of 5 Alpha-DHT (e.g., 5 Alpha-DHT undecanoate) formulations for oral use as a gelatin capsule containing 5 Alpha-DHT undecanoate.

In embodiments, the disclosure related to compositions and methods comprising 5 alpha dihydrotestosterone undecanoate as a fixed combination with 5 beta dihydrotestosterone undecanoate (e.g., for oral use as a gelatin capsule).

In some alternative embodiments of the disclosure, are provided pharmaceutical fixed dose compositions for topical application to enhance hair growth in patients in need thereof, or who are desirous thereof, that comprise an effective amount 5 Alpha-DHT with cyclopentane N-ethyl heptanamide-5-cis-2-(3α-hydroxy-5-phenyl-1-trans-pentenyl)-3,5-dihydroxy, [1α,2β,3α,5α], also known as bimatoprost, along with minoxidil.

Another aspect of the disclosure provides methods for decreasing the rate of scalp terminal hair follicle and hair loss of terminal hairs in human males, females, mammals and animals as well as stimulating the rate of scalp hair growth and for enhancing the conversion of vellus hair or intermediate hair to growth as terminal hair in a human or non-human by administering to the skin an effective amount of 5 Alpha-DHT, and one or more androgen receptor blocking agents, or 5 alpha reductase inhibitors such as, for example, bimatoprost and minoxidil. In some embodiments, the additional combination of such agents (e.g., bimatoprost and minoxidil) provides a synergistic effect when compared to one or both of bimatoprost and minoxidil.

In accordance with some aspects of the invention, the compound 5 Alpha dihydrotestosterone can be provided as 5 Alpha dihydrotestosterone undeconoate and may be used alone or in combination with other agents such as, for example, 5 alpha reductase inhibitors, androgen receptor blocker medications, bimatoprost and/or minoxidil. The agents can be formulated as mixtures with a dermatologically compatible vehicles or carriers. Exemplary vehicles in such compositions can comprise, for example, aqueous solutions such as e.g., physiological saline solutions, oil solutions or ointments. In some embodiments, the vehicle can further comprise dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts and matrices when the drug is to be administered.

What is claimed is:

1. A method of supportive treatment in female to male transgender males with gender dysphoria receiving gender affirming hormone therapy comprising topically administering a composition or pharmaceutical formulation of 5 Alpha Dihydrotestosterone (5 Alpha-DHT), or a pharmaceutically acceptable salt or ester thereof, to the patient in an amount effective to promote hair growth; and
    wherein the concentration of 5 Alpha-DHT in the composition or pharmaceutical formulation is selected from the group consisting of (i) ranges from about 0.00001% to about 50% weight to weight; (ii) ranges from 0.00001% to about 50%, weight to volume; and (iii) ranges from about 0.00001% to about 50%, volume to volume;
    wherein the method promotes hair growth on the face, body, or pubic region of the patient; and
    wherein the 5 Alpha-DHT composition or pharmaceutical formulation further comprises one or more dermal penetration enhancement agents that optimize hair follicle and hair shaft absorption when applied topically.

2. The method of claim 1, wherein the supportive treatment is part of a gender affirming therapy or a gender transitioning therapy.

3. The method of claim 1, wherein the patient is gay, intersex, plus (+) and/or non-binary.

4. The method of claim 1, wherein the composition or pharmaceutical formulation comprising 5 Alpha-DHT is used in patients with genetic androgen insensitivity and androgen resistance disorders.

5. The method of claim 1, wherein the gender affirming hormone therapy promotes or induces one or more physiological characteristics associated with the gender to which the patient is affirming or transitioning.

6. The method of claim 1, wherein the concentration of 5 Alpha-DHT in the composition or pharmaceutical formulation is about 0.05% to about 25% weight to weight, weight to volume or volume to volume.

7. The method of claim 1, wherein the administering of 5 Alpha-DHT is in combination with one or more other therapy.

8. The method according to claim 7, wherein the other therapy comprises a hormone therapy and/or surgery.

9. The method of claim 8, wherein the administering of 5 Alpha-DHT is used in combination with one or more of androgens, other hormones, active agents, surgery, and mental health support therapies.

10. The method of claim 9, wherein the administering of 5 Alpha-DHT improves or enhances hair growth of an existing concurrent pharmaceutical therapy comprising testosterone.

11. The method of claim 1, wherein the 5 Alpha-DHT is administered systemically, orally, topically, transmucosally, by injection, by suppository, transdermally, or by implant.

12. The method of claim 1, wherein the 5 Alpha-DHT is administered one or more times a day.

13. The method of claim 1, wherein the 5 Alpha-DHT is administered on an interval therapy dosing cycle comprising at least one period of administration and a period of non-administration.

14. The method of claim 13, wherein the interval therapy comprises an administration period of 1 or more weeks followed by at least 1 week of non-administration.

15. The method of claim 1, wherein the 5 Alpha-DHT comprises 5 Alpha-DHT undecanoate.

16. The method of claim 1, wherein the 5 Alpha-DHT is administered one or more times a week.

17. The method of claim 1, wherein the 5 Alpha-DHT is administered every other day.

\* \* \* \* \*